United States Patent
Piletsky et al.

(10) Patent No.: US 6,852,818 B1
(45) Date of Patent: Feb. 8, 2005

(54) MOLECULARLY IMPRINTED POLYMERS PRODUCED BY TEMPLATE POLYMERIZATION

(75) Inventors: Sergiy Anatoliyovich Piletsky, Cranfield (GB); Olena Volodimirivna Piletska, Cranfield (GB); Ganna Valentinivna Elska, Kiev (UA); Hakan Syen Andersson, Kalmar (SE); Ian Alan Nicholls, Kalmar (SE); Anthony Peter Francis Turner, North Crawley (GB)

(73) Assignee: Cranfield University, Bedfordshire (GB)

( * ) Notice: Subject to any disclaimer, the term of this patent is extended or adjusted under 35 U.S.C. 154(b) by 0 days.

(21) Appl. No.: 10/110,235

(22) PCT Filed: Oct. 23, 2000

(86) PCT No.: PCT/GB00/04085

§ 371 (c)(1),
(2), (4) Date: Sep. 23, 2002

(87) PCT Pub. No.: WO01/30856

PCT Pub. Date: May 3, 2001

(30) Foreign Application Priority Data

Oct. 23, 1999 (GB) .............................................. 9925056

(51) Int. Cl.⁷ .............................................. C08F 26/00
(52) U.S. Cl. .................................... 526/303.1; 526/319
(58) Field of Search .............................. 526/303.1, 319

(56) References Cited

U.S. PATENT DOCUMENTS 5,994,110 A   11/1999  Haupt et al.
6,018,018 A * 1/2000  Samuelson et al. ......... 528/422

OTHER PUBLICATIONS

Steinke et al., "A Simple polymerisable Carboxylic Acid Receptor: 2–acrylamido pyridine", Trends in Analytical Chemistry, 18(3), 159–164 (1999).*
J.H.G. Steinke et al.: "A simple polymerisable carboxylic acid receptor: 2–acrylamido pyridine" Trac. Trends in Analytical Chemistry, vol. 18, No. 3, pp. 159–164 03/99.
K. Ohkubo et al.: "Molecular design of transition–state analogue–impringed polymer catalysts–stereoselective esterolysis of amino acid esters". Kobunshi Ronbunshu (Japanese Polymer Science and Technology), vol. 52, No. 10, pp. 644–649 1995 (with English translation).

* cited by examiner

Primary Examiner—Ling-Siu Choi
(74) Attorney, Agent, or Firm—Oblon, Spivak, McClelland, Maier & Neustadt, P.C.

(57) ABSTRACT

A polymer (e.g. a peptide) is produced by polymerizing monomers in the presence of a template, particularly a biologically active molecule or sample. The polymer is extracted and a soluble (preferably water-soluble) fraction is derived which specifically binds the template. Thus it can have complementary activity (e.g. biological). Applications include therapy, detection systems and separation systems.

28 Claims, 4 Drawing Sheets

MOLECULARLY IMPRINTED POLYMERS PRODUCED BY TEMPLATE POLYMERIZATION

TECHNICAL FIELD

The present invention relates to molecularly imprinted polymers ("MIPs"), template polymerisation processes for their preparation, and uses thereof. In preferred embodiments the MIPs are biologically active, e.g. as drugs, effectors, modulators or inhibitors. Unless the context requires otherwise, "polymer" includes dimers, oligomers and higher polymers, and mixtures.

BACKGROUND ART

In template polymerisation, the formation of a polymeric receptor (replica or MIP) proceeds in the presence of another polymer or small-molecular weight organic substance (template). Prior to the initiation of polymerisation, and during polymerisation, the components (generally monomers) spatially distribute themselves (self-assembling process) around the template molecules in accordance with the size, polarity and functionality of the template. The monomers are polymerised into either linear chains or rigid three-dimensional networks.

The first example of silicic acid polycondensation in the presence of organic templates was presented by Polyakov and co-authors (see ref. 10–12, 19). Silica gels, prepared in their experiments retained structures, specific for those of template molecules.

Later experiments with templates, or molecular imprinting polymerisation, based on vinyl or acrylic monomers has been carried out in the groups of Wulff and Mosbach (see ref. 2, 5, 13, 16–18). Several patents describing the preparation of sorbents, catalysts and sensors, based on imprinted polymers were issued recently (see U.S. Pat. Nos. 5,110,833, 5,630,978, 5,728,296, 5,756,717, WO 9641173).

Another approach includes modification of proteins, such as enzymes, in the presence of template molecules to produce changes in their properties, e.g. specificity and activity (see ref. 1 and DE patent 19627162).

The traditional approach involves the production of highly cross-linked imprinted polymers, which are insoluble in water and organic solvents. Because of their inherent insolubility, the possibility to use these materials in pharmacology and medicine is restricted. Background material can be found in the following references.

1. Dabulis, K., et al., "Molecular Imprinting of Proteins and other Macromolecules Resulting in New Adsorbents," Biotechnol. Bioeng., 39(2):176–185 (1992).
2. Haupt, K., Dzgoev A., and K. Mosbach. Assay System for the Herbicide 2,4-D Using a Molecularly-Imprinted Polymer as an Artificial Recognition Element. Anal. Chem. 70, 628–631 (1998).
3. Holliger, P., et al., "Artificial Antibodies and Enzymes: Mimicking Nature and Beyond," Trends in Biotechnology, 13(1):7–9 (1995).
4. Illman, D., "Polymer Mimics Antibody in Drug Assay," Chemical & Engineering News, 71(9):30–31 (1993).
5. Mosbach, K., "Molecular Imprinting," Trends in Biochem. Sci., 19(1):9–14 (January 1994).
6. Noronha-Blob, L. et al., "Uptake and Fate of Water-Soluble, Nondegradable Polymers with Antiviral Activity in Cells and Animals," J. Med. Chem., 20(3):356–359 (1977).
7. Ottenbrite, R. M., et al., "Macrophage Activation by a Series of Unique Polyanionic Polymers," J. Macromol. Sci. Chem., H. K. Frensdorff, ed., A25(5–7):873–893 (1988).
8. Ottenbrite, R. M., "Introduction to Polymers in Biology and Medicine," in Anionic Polymeric Drugs (Polym. Biol. Med.), L. G. Donaruma, R. M. Ottenbrite, and O. Vogl, eds., John Wiley & Sons, New York, vol. 1, pp. 1–20 (1980).
9. Piletsky, S. A., et al. Optical detection system for triazine based on molecularly-imprinted polymers. Anal. Lett. 30, 445–455 (1997).
10. Polyakov, M V. Adsorption properties and structure of silica gel. Zhur. Fiz. Khim. 2, p.799. (1931).
11. Polyakov, M. V., L. P. Kuleshina, and I. E. Neimark. On the dependence of silica gel adsorption properties on the character of its porosity. Zhur. Fiz. Khim.10:100–112 (1937).
12. Polyakov, M. V., P. M. Stadnik, M. W. Paryckij, I. M. Malkin, and F. S. Duchina. On the structure of silica. Zhur. Fiz. Khim. 4, p. 454 (1933).
13. Ramström, O., Ye L., and Mosbach K. Artificial Antibodies to Corticosteroids Prepared by Molecular Imprinting. Chem. & Biol. 3 (6):471–477 (1996).
14. Shea, K. J., et al., "Molecular Recognition on Synthetic Amorphous Surfaces. The Influence of Functional Group Positioning on the Effectiveness of Molecular Recognition," J. Am. Chem. Soc., 108(5):1091–1093 (1986).
15. Tahmassebi, D. C., et al., "Molecular Imprinting Synthesis of a 3-Helix Bundle Proteins on Modified Silica Gel," Abstr. Pap. Am. Chem. Soc., vol. 204, No. 1–2:314, 204$^{th}$ American Chemical Society National Meeting, Washington, D.C. (Aug. 23–28, 1992).
16. Vlatakis, G., et al., "Drug Assay Using Antibody Mimics Made by Molecular Imprinting," Nature, 361(18) :645–647 (1993).
17. Wulff, G., "Molecular Imprinting in Synthetic Polymers, Models for the Receptor Site in Enzymes," Makromol. Chem., Macromol. Symp., 70/71:285–288 (1993).
18. Wulff, G., et al., "Enzyme-Analogue Built Polymers, 26: Enantioselective Synthesis of Amino Acids Using Polymers Possessing Chiral Cavities Obtained by an Imprinting Procedure with Template Molecules," Makromol. Chem., H.-G. Elias, T. Tsuruta, eds., 190(7):1727–1735 (1989).
19. Vysotskii, Z. Z., and M. V. Polyakov. The preparation of specific adsorbents. Zhur. Fiz. Khim. 30:1901–1902 (1956).

DISCLOSURE OF INVENTION

In a first aspect the invention provides a process comprising the steps of a) effecting template-directed polymerisation of functional monomers in the presence of a molecular template, thereby producing a polymer whereof at least a part is complementary to at least a part of the template; and b) preparation of a solution of a soluble polymer which is or is derived from said complementary polymer and which comprises at least a part which is complementary to at least a part of the template.

The resulting solution contains one or more species selected from polymers, oligomers and dimers which may be adapted to bind to the template molecule.

The template may be a molecule or a larger, generally biological, system. It is preferably a biological receptor, nucleic acid, cell, virus, microorganism, tissue sample, carbohydrate, oligosaccharide, polysaccharide, nucleoprotein, mucoprotein, lipoprotein, synthetic protein, glycoprotein, glucosaminoglycan, enzyme, steroid, immunosuppressant, hormone, heparin, antibiotic, vitamin or drug. It suitably has an absolute molecular weight from two hundred to three million.

Preferably the soluble polymer of step (b) has biological activity, e.g. as a drug, effector, modulator or inhibitor. Preferably the polymer is water-soluble, e.g. to a sufficient extent for showing biological activity in an aqueous medium.

Possible functional monomers include vinyl monomers, allyl monomers, acetylenes, acrylates, methacrylates, amino acids, nucleosides, nucleotides, carbohydrates, phenols, heterocycles, aniline, and their derivatives. Preferred monomers are water-soluble.

Polymerisation can be effected using conditions appropriate to the monomers, e.g. free radical initiators for ethylenically unsaturated monomers; condensing agents such as carbodiimides for amino acids; polymerase enzymes for nucleosides and nucleotides. When appropriate, cross-linking agents can be used.

Step (b) may comprise (i) separating from the polymerisation system a complex comprising the template molecule and complementary polymer; and (ii) removal of the template molecule. The separation of the complex may be achieved by change in pH of the solution, change in ionic strength of the solution, and/or adding urea, guanidine, or a substance which interacts with the template stronger than does the polymer.

The removal of the template may be achieved by filtration, electrophoresis, chromatographic separation, washing or centrifugation.

Preparation of the solution may involve appropriate solution and separation of the solution from insoluble particles. Thereafter the solubilised synthesized molecules may be fractioned and/or purified, e.g. by centrifugation, chromatography, electrophoresis or dialysis.

In a preferred type of embodiment the MIP is a linear polymer formed from a set of different functional monomers, e.g. amino acids or nucleosides or nucleotides. The nature of the MIP may then be determined by its sequence. Steps (a) and (b) may then be followed by (c) sequence determination and optionally (d) synthesis of MIPs having all or part of the determined sequence and/or variants thereof.

A MIP of the present invention may be used as a drug in pharmacology and medicine, as a receptor-specific ligand in analytical chemistry or for use in performing separations in biotechnology, or the pharmaceutical and food industries.

The present invention makes available a method for the synthesis of biologically active molecules (drugs, effectors, modulators, inhibitors) using template polymerisation and their application in analytical chemistry, pharmacology, medicine and the food, biotechnology and pharmaceutical industries. Specifically, biologically-active molecules may be synthesized by: a) polymerisation of functional monomers around a biological receptor, enzyme, nucleic acid, cell, virus, micro organism, tissue sample or drug; b) separation of the polymer-template complex formed, and removal of the template molecule; c) if necessary, solubilisation of the synthesized replica. This approach differs from the method described in WO patent 9640822 and U.S. Pat. No. 5,630,978, where biologically-active molecules were prepared in the presence of template-imprinted polymer, which had been prepared in the presence of another template, normally a drug such as heparin. The resulting replica resembles the structure of the original drug molecule. It can hardly be expected that the activity of molecules synthesized in this way can be more pronounced than that of the original template.

In the method described here, the synthesized molecules have a structure complementary to that of the original template and have the ability to bind it with reasonably high affinity. These synthetic molecules, in particular polymers, have predetermined affinities and specificities superior to those of randomly synthesized polymers and can be prepared much more easily than specifically designed discrete organic structures (see ref. 6–8). Molecules synthesized as described in this invention (dimers, oligomers, polymers, or their mixture) can be used as drugs in pharmacology and medicine, as receptor-specific ligands in analytical chemistry (sensors, assays), and for separations in the biotechnology, pharmaceutical and food industries. Previous efforts in drugs design have typically been based upon the cumbersome investigation of structure-activity relationships of large numbers of chemical structures. The present invention describes a more simple and direct method to design a biologically-active substance, which should be of great benefit in comparison with traditional drugs design and discovery methods.

MODES FOR CARRYING OUT THE INVENTION

Figure 1:
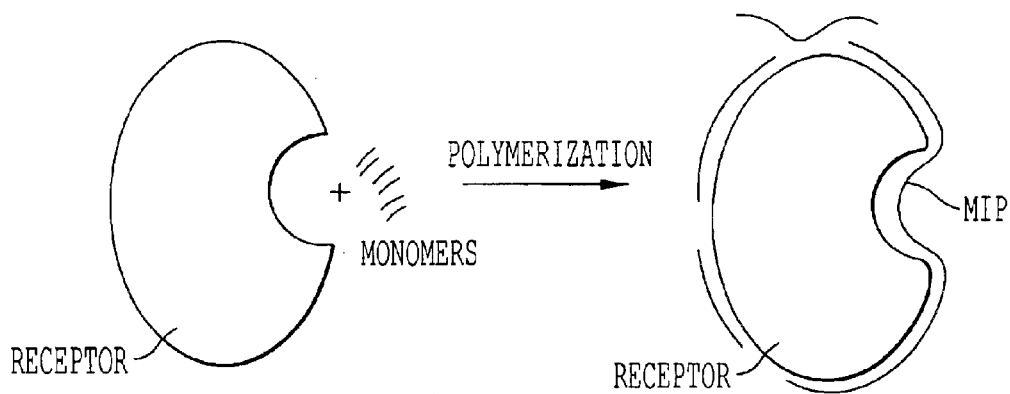
FIG. 1 depicts a scheme of the template polymerisation in the presence of a template-receptor. Template-specific polymer-MIP is formed in three steps 1) self-assembly of monomers around the receptor surface; 2) polymerisation of monomers by radical polymerisation, anion or cation polymerisation or polycondensation; 3) separation of template-polymer complex and replica solubilisation (not shown).

Traditional template polymerisation includes the formation of a rigid polymer network around small organic substances, such as drugs. Molecularly imprinted polymers (MIPs) prepared in this way resemble synthetic mimics of natural receptors, specific for the drug molecule used as the template. Using this approach, the polymers resulting from the use of large molecules, such as proteins and enzymes, also yield insoluble polymeric products devoid of biological activity.

The present invention describes the formation of soluble MIPs, prepared in the presence of a template, in particular large molecules such as receptors, enzyme or nucleic acids. In contrast to the traditional approach to MIP preparation, polymers prepared in this way resemble effectors (activator, inhibitor or substrate) of the template, and can have biological activity. Such polymers can be used, for example, as drugs in pharmacology and medicine. In the text describing the present invention the terms "biologically-active substances" "replica molecules" and "MIPs" have the same meaning.

The first embodiment describes the preparation of the biologically-active molecules (MIPs) in the presence of a template which is a biological receptor, nucleic acid, cell, virus, microorganism, tissue sample, carbohydrate, oligosaccharide, polysaccharide, nucleoprotein, mucoprotein, lipoprotein, synthetic protein, glycoprotein, glucosaminoglycan, steroid, immunosuppressant, hormone, heparin, antibiotic, vitamin or drug.

Normally, a template soluble in an appropriate solvent, preferably water, is mixed together with functional monomers, one of which can be a crosslinker, and an initiator. Polymerisation can be initiated by heating or UV irradiation and normally takes 1–24 h.

The second embodiment describes monomers which can be used for MIP preparation, and includes: vinyl monomers, allyl monomers, acetylenes, acrylates, methacrylates, amino acids, nucleosides, nucleotides, carbohydrates, phenols, heterocycles, aniline, and their derivatives. Crosslinking monomers can also be used if it is necessary to fix or stabilize the structure of the resulting replica molecule, so that it remains complementary to that of the template. Methylene bisacrylamide (BAA) and N,N'-bisacryloylpiperazine (BAP), which are soluble in water, can be used in this context.

The separation of the complex formed between the template and replica molecules, and the solubilisation of the synthesized biologically-active polymeric molecules can be achieved by polymer grinding, by change in solution pH, in ionic strength, or through the addition of urea, guanidine, or substances which interact with the template stronger than the replica, filtration, electrophoresis, chromatographic separation, washing, centrifugation or dialysis. This step is necessary in order to prepare a water- or organic solvent soluble fraction of MIP which has high affinity to the template and can interact with template in order to activate or inhibit its interaction with other molecules in vitro or in vivo.

The last embodiment describes the application of the synthesized biologically-active molecules as drugs in pharmacology and medicine, as receptor-specific ligands in analytical chemistry (for use as recognition components in sensors, or in assays), or for separations in the biotechnology, pharmaceutical and food industries. The present invention will now be further particularly described with reference to the following, non-limited examples.

1. Synthesis of a Water-Doluble MIP with Specificity to D1 Protein—Natural Herbicide Receptor.
a) Preparation of D1 Protein Mature green pea leaves were collected and washed in distilled water, dried with filter paper and frozen in liquid nitrogen. Frozen leaves were placed in a 50 ml centrifuge tube with cold isolation buffer containing 0.4M saccharose, 50 mM Tris-HCl, pH 8.0, 10 mM NaCl. The leaves were homogenized in Psyscotron homogenizator with 3–5 sec bursts at high speed. This homogenate was filtered through two sieves (Mesh No. 32, 20) without squeezing and centrifuged at 1 000 g for 15 min at 4° C.

The pellet was resuspended in wash-buffer (50 mM Tris-HCl, pH 8.0, 10 mM NaCl) and centrifuged under the same conditions. This step was repeated twice, then the pellet containing the chloroplast membranes was homogenized with a small amount of wash-buffer and sonificated in a pre-cooled ultrasonic bath for 30 min at full output. The suspension was mixed and shaken with an equal volume of cold n-butanol (−20° C.). Phases were separated by centrifugation at 1 000 g for 5 min. Water phase containing proteins was collected. The separation of proteins and lipids was improved by repeating this step three times.

The crude D1 protein was further purified by reverse-phase chromatography. The chromatography was performed on a C18 column with linear gradient of iso-propanol (0–30%) in 50 mM Tris-HCl, pH 8.0. The D1 protein was eluted at high concentration of iso-propanol, lyophilized and stored at −20° C.

b) MIP Synthesis 10 mg of lyophilized D1 protein was extracted three times with 1 ml hexane to remove plastoquinone from the herbicide-binding site, mixed with 194 mg bisacryloylpiperazine (BAP) or 60 mg of methylene bisacrylamide (BAA), 6.9 mg urocanic acid, 10 mg ammonium persulfate and dissolved in 200 $\mu$l $H_2O$. Polymerisation was initiated by adding 2 $\mu$l of 30% TEMED solution and proceeded at 80° C. during 12 h. The resulting polymer was then washed from the template by 0.1 M HCl, carefully ground and filtered through a glass filter. The filtrate was collected and concentrated using a rotor evaporator. Control (blank) polymer was prepared in the same way, but in absence of D1 protein. The concentrated polymer solutions were centrifuged through macrofilters (Ultra-Spin Macrofilter, Roth, Germany) separating molecules with molecular weight <5 kDa, 5–10 kDa and >10 kDa. The optical densities of all solutions were measured at 260 nm and adjusted with distilled water to equal value for the analyses.

2. Analysis of the Polymers' Affinity.
a) Preparation of Affinity Column with Immobilized D1 Protein (D1-Column).

5 g CH—Sepharose 4B with free carboxylic groups (Pharmacia Fine Chemicals) was soaked in 0.01 M phosphate buffer pH 7.5. 100 mg D1 protein with extracted plastoquinone were dissolved in the same buffers containing 1 mM morpholine ethane carbodiimide and 0.1 mM N-hydroxysuccinimide, added to the sepharose and left overnight at +4° C. The column with immobilized D1 protein was washed with 5 volumes of 25 mM phosphate buffer pH 7.5 and stored at +4° C. before use.

b) Chromatography of the BAP-Based MIPs on D1-Column.

Figure 2:
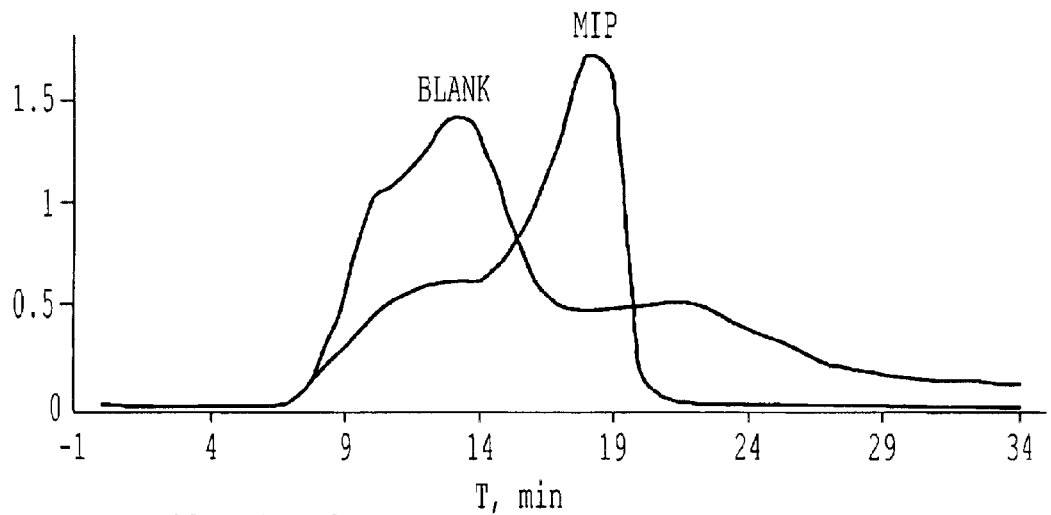
FIG. 2 depicts a chromatographic response from a BAP-based polymer column with immobilized D1 protein in 25 mM sodium phosphate buffer, pH 7.5. Flow rate 0.3 ml/min. Injections—300 $\mu$l of the polymer solution with concentration 1 mg/ml. Blank—nonimprinted polymer; MIP—imprinted polymer.

The column was equilibrated with eluent (25 mM sodium-phosphate buffer, pH 7.5) running at flow rate 0.3 ml/min at room temperature. Polymer solution in the eluent was injected into the column and the retention times and areas of the peaks were measured. Elution profiles of the MIP and blank polymers on the D1-column are presented in FIG. 2.

Elution of non-interacting sample-BAP was observed at 9 min. Capacity factors for blank and imprinted polymers are:

$K_{Blank}$=0.56(300 µl); after 5 days $K_{Blank}$=0.71(30 µl)

$K_{MIP}$=1.11(300 µl); after 5 days $K_{MIP}$=1.0(30 µl)

The retention times change with time due either to polymer conformational changes or partial polymer hydrolysis. The separation factors for the MIP and Blank polymers varies in these experiments from α=1.98 to α=1.41. In all cases the imprinted polymers had much stronger affinity to the D1-column than to the blank polymer.

c) Chromatography of the BAA-Based MIPs on D1-Column.

Figure 3:
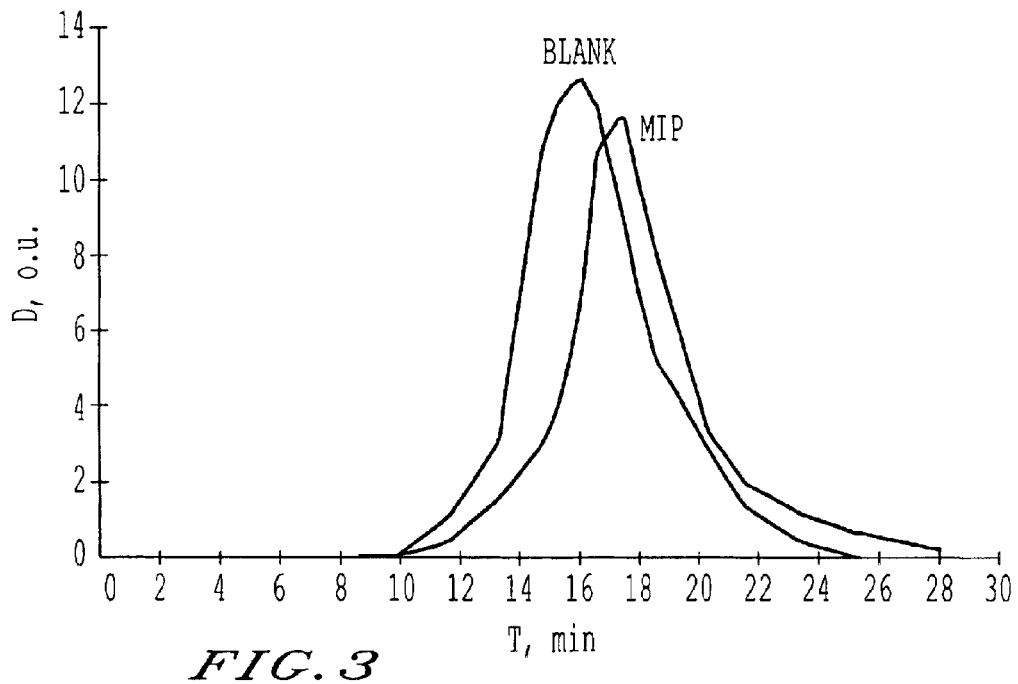
FIG. 3 depicts a chromatographic response from BAA-based polymers on the D1-column in 25 mM sodium phosphate buffer, pH 7.5. Flow rate 0.3 ml/min. Injections—300 $\mu$l of the polymer solution with concentration 1 mg/ml. Blank—nonimprinted polymer; MIP—imprinted polymer.

The column was equilibrated with eluent (25 mM sodium-phosphate buffer, pH 7.5) running at flow rate 0.3 ml/min at room temperature. A polymer solution of the eluent was injected onto the column and retention times and areas of the peaks were measured. Elution profiles of the MIP and Blank polymers on the D1-column are presented in FIG. 3. Elution of non-interacting sample-BAP was observed at 10 min. Capacity factors for blank and imprinted polymers are:

$K_{Blank}$=0.6(300 µl); $K_{MIP}$=0.8(300 µl).

No changes in elution times for the polymers was observed. The separation factor for MIP and Blank polymers was determined in these experiments as α=1.33. Again, the imprinted polymer had much stronger affinity to the D1-column than to the blank polymer.

3. Analysis of the Biological Activity of the Polymers Synthesized. Influence of the Polymers on the Activity of Thylakoid Membranes.

Thylakoid membranes were diluted to 30 µg chlorophyll ml$^{-1}$ with buffer (0.35 M saccharose, 10 mM NaCl, 50 mM Tris-HCl, pH 7.5, 1% BSA). Samples containing 30 µl of a thylakoid membrane solution (1 µg chlorophyll in probe) containing sucrose (0.35 M) and BSA (1%) was mixed with polymer solution (20 µl), and DPIP (100 µl, 0.3 mM) in Tris-HCl buffer (0.1 M, pH 7.5) in the microplate wells. The samples were illuminated for 10 min with a 100 W lamp and the absorbance was measured at 530 nm using a Dinatech reader (Germany). The activity of thylakoid membrane preparations was calculated from the data on the amount of reduced DPIP, concentration of chlorophyll and the time of illumination.

Figure 4:
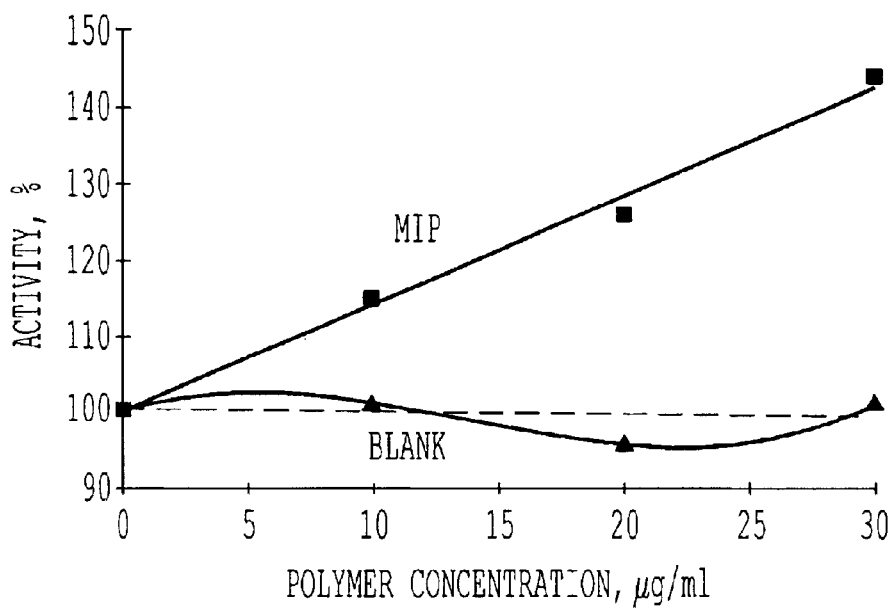
FIG. 4 depicts the influence of the BAP-based polymers on in vitro chloroplast activity. Reaction mixture (300 $\mu$l volume) contains: chloroplast suspension (1 $\mu$g chlorophyll) and 9 $\mu$g DPIP in 0,1 M sodium phosphate buffer, pH 7.5.
Figure 5:
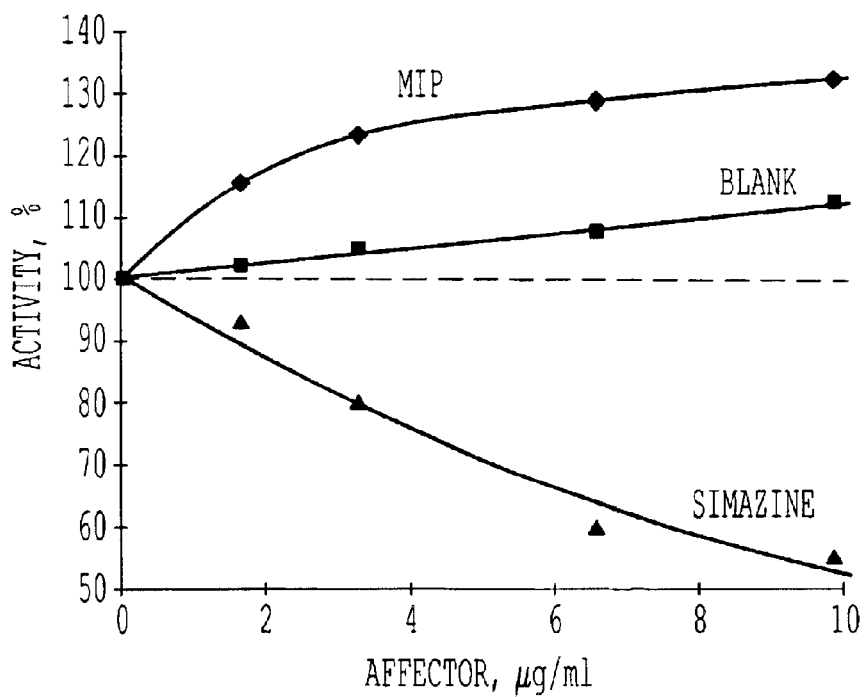
FIG. 5 depicts the influence of the BAA-based polymers on in vitro chloroplast activity. Reaction mixture (300 $\mu$l volume) contains: chloroplast suspension (1 $\mu$g chlorophyll) and 9 $\mu$g DPIP in 0,1 M sodium phosphate buffer, pH 7.5.
Figure 6:
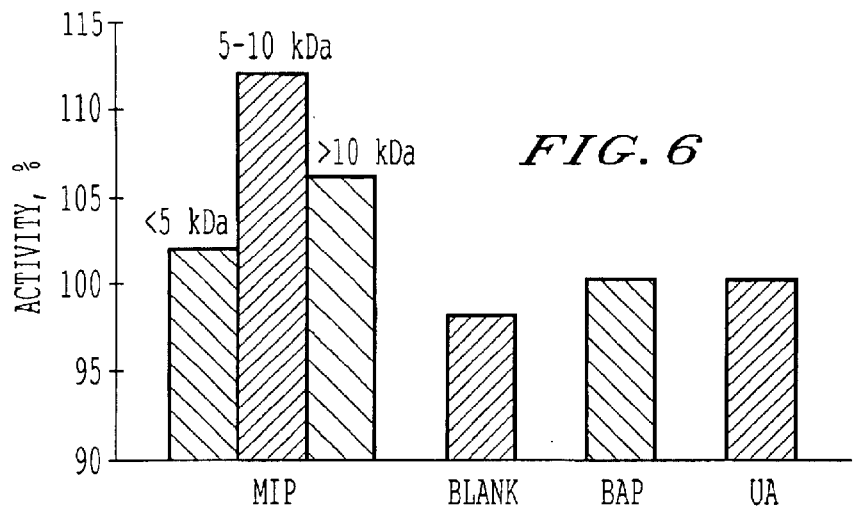
FIG. 6 depicts the influence of the size of the polymer fractions (BAP-based polymers) and monomers—BAP and urocanic acid (UA) on the chloroplast activity. Blank—fraction of the Blank polymer with size 5–10 kDa. Reaction conditions the same as above.

It was shown that MIP gave a clear increase (up to 45% for 30 µg/ml of polymer concentration) in thylakoids activity (FIG. 4 and FIG. 5). Practically no effect has been observed for Blank polymer and individual monomers. The effect is opposite to these demonstrated by herbicides—synthetic inhibitors of D1 (FIG. 5). It is interesting that fractions with different sizes have different activity. The best results were obtained for 5–10 kDa fraction which indicate that in order to possess biological activity MIPs have to have an optimal size. Too small or too large particles will be not able to demonstrate biological effect.

4. Synthesis and Investigation of Peptide Ligands, Specific for Glycosylated Haemoglobin.

Purified glycosylated haemoglobin (HbA$_{1c}$, 4 mg) in 2 ml of 50 mM sodium phosphate buffer pH 7.5 was mixed with 2.5 ml solution of 20 natural amino acids (2 mM each). 0.5 ml of 220 mM solution of 1-ethyl-3-(3-dimethylaminopropyl) carbodiimide (EDC) was added to the reaction vessel. The amino acid polymerisation in the presence of template was carried out for 4 hours. To prepare blank polymer, the same reaction was performed in the absence of haemoglobin. To remove EDC, non-reacted amino acids and low-affinity peptides, the reaction mixture was filtered through 50 kDa permeative Amicon membranes (Centriplus YM-50, Millipore). The haemoglobin, concentrated on the filter was washed twice with 50 mM sodium phosphate buffer.

Hydrochloric acid was used to remove peptides from the imprinted haemoglobin. 10 µl of 5 M HCl was added to 2 ml haemoglobin solution shifting the pH to pH 3.0. The mixture was sonicated for 10 min and filtered through a 50 kDa Amicon membrane again. Peptides, which passed through membrane this time were collected. The solution was adjusted with 5 µl of 4 M sodium hydroxide to pH 7.5.

The affinity of the synthesised peptides was measured using the technique of Surface Plasmon Resonanse (SPR). The HbA$_{1c}$ and HbAo were linked via a peptide condensation using EDC/NHS chemistry with CM5 Biacore chip (Biacore, Uppsala, Sweden). The level of haemoglobin immobilisation was 1000 RU and 7000 RU, correspondingly. Despite the significant difference in immobilisation level it was shown that MIPs have slightly stronger affinity to HbA$_{1c}$ surface (data not shown).

Figure 7A:
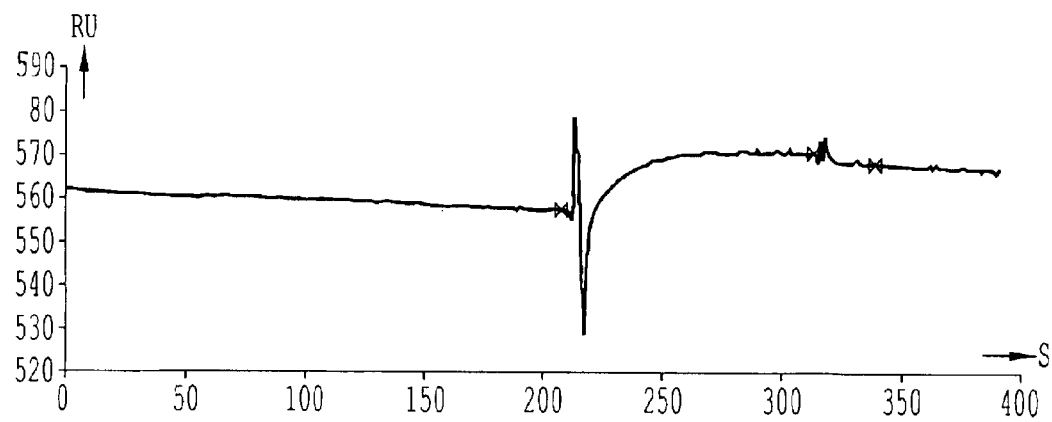
FIG. 7 (*a*), (*b*) and (*c*) are surface plasmon resonance spectra showing the binding of MIP peptides to glycosylated and unglycosylated haemoglobin and BSA, respectively.
Figure 7B:
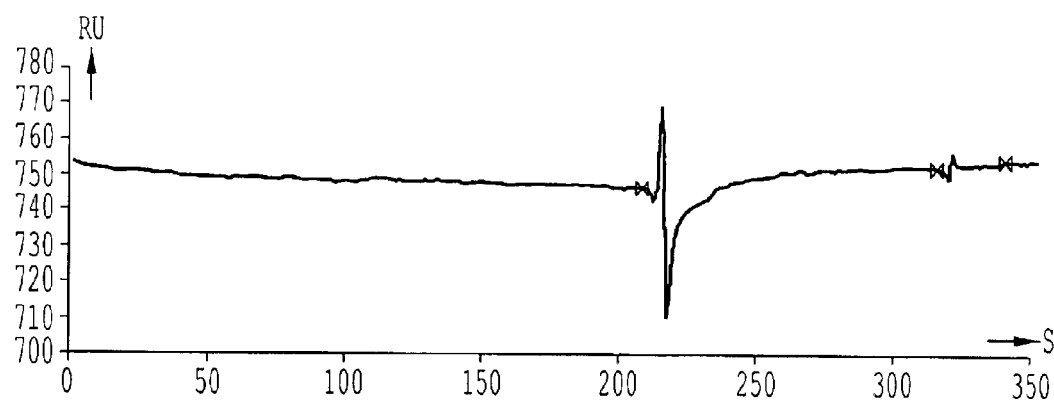
Figure 7C:
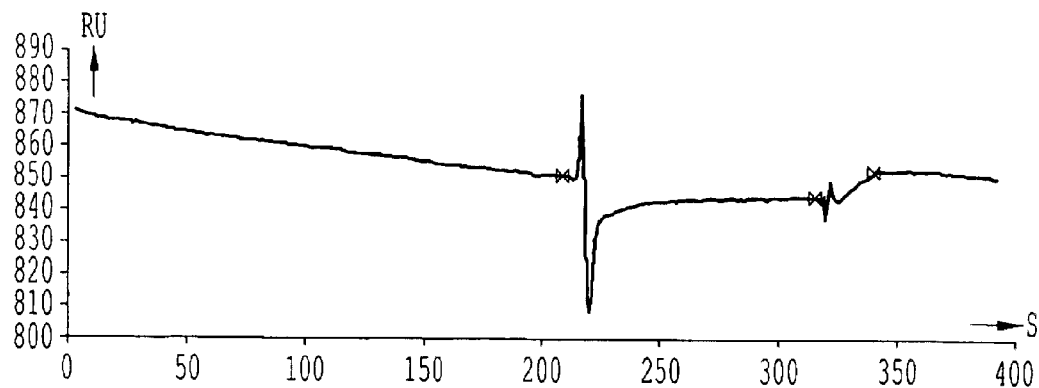

In order to improve the specificity of the MIPs for glycosylated haemoglobin, 3 mg of the HbA$_0$ was added to 2 ml of the peptide solution in 50 mM sodium phosphate buffer, pH 7.5 and incubated for 1 h at room temperature. The HbA$_0$ with bound peptides was removed by filtration using a 50 kDa Amicon membrane to eliminate the peptides which were non-specific for HbA$_{1c}$. The fraction containing peptides possessing affinity for HbA$_{1c}$, only was analysed using the Biacore. HbA$_{1c}$, HbA$_0$ and BSA were immobilised on CM5 Biacore chip with possibly equal immobilisation level (1100 RU, 1050 RU and 1020 RU, correspondingly) to estimate the selectivity of the extracted MIP peptides. The binding analysis indicates clearly that the affinity of post-screened fraction for HbA$_{1c}$, was increased in comparison with pre-screened one (see FIG. 7). The binding with the HbA$_{1c}$, surface was estimated as 12.5 RU, with HbA$_0$ —5.9 RU and 0 for BSA.

The results indicate that amino acids can be used as monomers in imprinting polymerisation. Synthesised MIPs have enhanced specificity and affinity to the template as compared with random synthesised (blank) polymers.

5. Synthesis and Investigation of Peptide Ligands, Specific for Yeast.

4 mg purified yeast membranes (*Sporobolomyces roseus*) in 2 ml of 50 mM sodium phosphate buffer pH 7.5 were mixed with 2.5 ml solution of 20 natural amino acids (2 mM each). 0.5 ml of 220 mM solution of 1-ethyl-3-(3-dimethylaminopropyl)carbodiimide (EDC) was added to the reaction vessel. The amino acid polymerisation in the presence of template was carried out for 4 hours. To prepare blank polymer, the same reaction was performed in the absence of template. To remove EDC, non-reacted amino acids and low-affinity peptides, the reaction mixture was filtered through 50 kDa permeative Amicon membranes (Centriplus YM-50, Millipore). The cell membranes, concentrated on the filter were washed twice with 50 mM sodium phosphate buffer.

Hydrochloric acid was used to remove peptides adsorbed onto the yeast membrane. 10 µl of 5 M HCl was added to 2 ml yeast membranes solution shifting the pH to pH 3.0. The mixture was sonicated for 10 min and filtered through a 50 kDa Amicon membrane again. Peptides, which passed through membrane this time were collected. The solution was adjusted with 5 µl of 4 M sodium hydroxide to pH 7.5.

Figure 8:
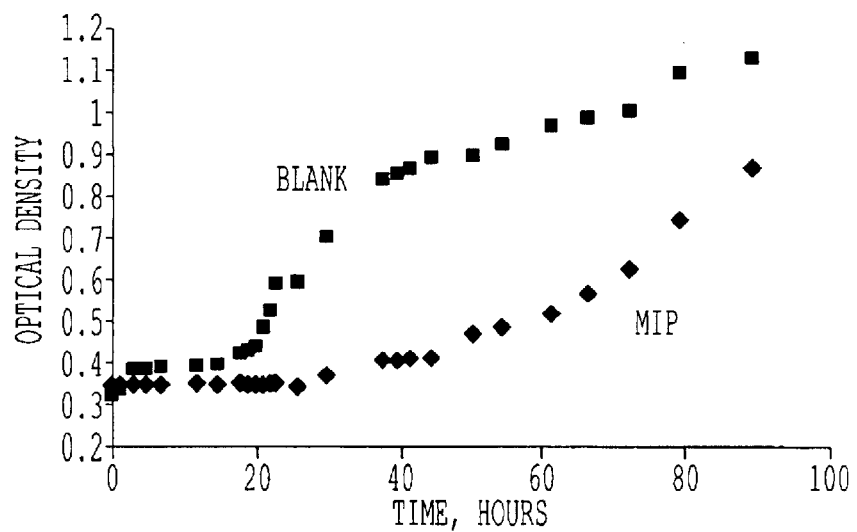
FIG. 8 is a graph of optical density v. time, showing the growth of a yeast in the presence of a blank peptide or a peptide MIP complementary to yeast membranes.

Synthesised peptides were added to media with yeast in concentrations of 0.6, 6, 25, 50, 100 µg/ml. The yeast growth was monitored by measuring optical density of the culture at 405 nm. The influence of the synthesised peptides on the growth process is presented in FIG. 8. The inhibition, observed for MIP peptides is a clear indication of their biological activity. The nature of this phenomenon could be explained by specific inhibition of the receptors exposed on the membrane surface by MIP peptides. It is important that this effect was much more pronounced in the case of yeast membranes in comparison with *E. Coli* or *bacillus* species which indicates its specificity. No change in yeast growth was observed in the presence of blank peptides.

6. Synthesis and Investigation of Peptide Ligands Prepared in the Presence of Trypsin.

Figure 9:
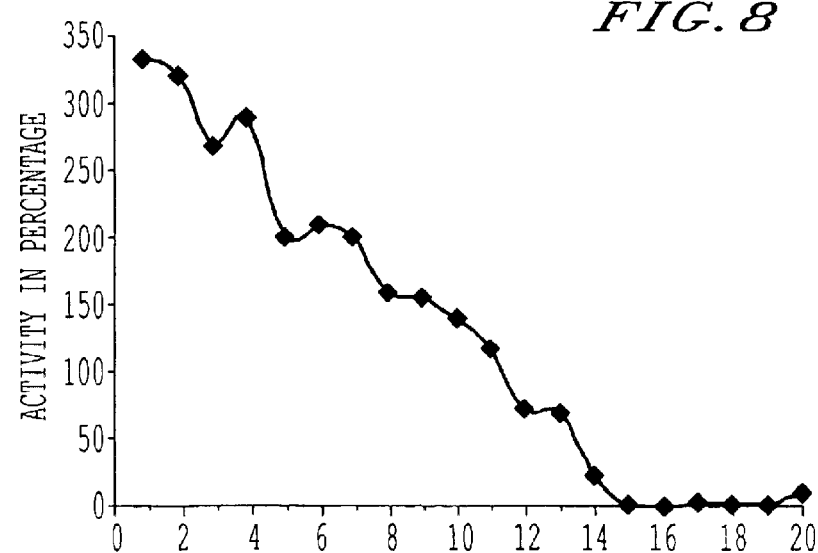
FIG. 9 is a graph showing trypsin activity as influenced by fractionated MIP peptides.

4 mg of trypsin in 2 ml of 50 mM sodium phosphate buffer pH 7.5 was mixed with 2.5 ml solution of 20 natural amino acids (2 mM each). 0.5 ml of 220 mM solution of 1-ethyl-3-(3-dimethylaminopropyl)carbodiimide (EDC) was added to the reaction vessel. The amino acid polymerisation in the presence of template was carried out for 4 hours. To prepare blank polymer, the same reaction was performed in the absence of template. To remove EDC, non-reacted amino acids and low-affinity peptides, the pH of reaction mixture was adjusted to 3.0 by adding hydrochloric acid aliquot. The mixture was immediately injected into HPLC and separated using Superdex Peptide column in 10 mM sodium phosphate saline buffer, pH 7.4. The influence of peptide fractions on trypsin activity was analysed (FIG. 9). It is important that only first three fractions had enzymatic activity which originated from the residual quantities of trypsin presented in the solution. The rest of the fractions did not have trypsin enzymatic activity on their own but they were able to activate substantially the trypsin added to them. The effect could be explained by partial stabilization of the trypsin structure in the presence of imprinted peptides.

What is claimed is:

1. A process comprising the steps of
   a) providing a mixture of different functional monomers;
   b) effecting template-directed polymerisation of functional monomers of said mixture in the presence of a molecular template, thereby producing a linear copolymer wherein at least a part of said linear copolymer is formed from a sequence of said monomers such that it is complementary to at least a part of the template; with the proviso that if the template is a nucleic acid, the monomers comprise species other than nucleotides;
   c) preparation of a solution of a soluble polymer which is or is derived from said linear copolymer and which comprises at least a part which is complementary to at least a part of the template; and
   d) sequence determination.

2. A process according to claim 1, wherein the template is a biological receptor, nucleic acid, cell, virus, microorganism, tissue sample, carbohydrate, oligosaccharide, polysaccharide, nucleoprotein, mucoprotein, lipoprotein, synthetic protein, glycoprotein, glycosaminoglycan, enzyme, steroid, immunosuppressant, hormone, heparin, antibiotic, vitamin or drug.

3. A process according to claim 1, wherein the template is a molecular species having a molecular weight of 200–3,000,000.

4. A process according to claim 1, wherein the functional monomers are one or more compounds selected from the group consisting of vinyl monomers, allyl monomers, acetylenes, acrylates, methacrylates, amino acids, nucleosides, nucleotides, carbohydrates, phenols, heterocycles, and aniline, or derivatives thereof.

5. A process according to claim 1, wherein the functional monomers are selected from the group consisting of amino acids, nucleosides and nucleotides.

6. A process according to claim 1, wherein the functional monomers comprise amino acids and polymerisation is effected by means of an amide-generating condensing agent.

7. A process according to claim 1, in which step (b) comprises (i) separating from the polymerisation system a complex comprising the template molecule and said linear copolymer; and (ii) removal of the template molecule.

8. A process according to claim 7, wherein removal of the template involves separation of the template from the polymer by means of one or more of change in pH of the solution, change in ionic strength of the solution, and/or adding urea, guanidine, or a substance which interacts with the template stronger than does the polymer.

9. A process according to claim 7, wherein removal of the template employs one or more of filtration, electrophoresis, chromatographic separation, washing or centrifugation.

10. A process according to claim 1, wherein step (d) is followed by step (e) synthesis of polymers having all or part of the determined sequence and/or variants thereof.

11. A method of making a drug comprising the process of claim 1.

12. A method of making a receptor-specific ligand comprising the process of claim 1.

13. A method comprising admixing a linear copolymer obtained by the process of claim 1 with a pharmaceutical composition.

14. A method comprising admixing a linear copolymer obtained by the process of claim 1 with a food.

15. A process comprising the steps of
   a) providing a mixture of different functional monomers, wherein the functional monomers are one or more compounds selected from the group consisting of vinyl monomers, allyl monomers, acetylenes, acrylates, methacrylates, amino acids, nucleosides, nucleotides, carbohydrates, and heterocycles, or derivatives thereof;
   b) effecting template-directed polymerisation of functional monomers of said mixture in the presence of a molecular template, thereby producing a linear copolymer wherein at least a part of said linear copolymer is formed from a sequence of said monomers such that it is complementary to at least a part of the template; with the proviso that if the template is a nucleic acid, the monomers comprise species other than nucleotides; and
   c) preparation of a solution of a soluble polymer which is or is derived from said linear copolymer and which comprises at least a part which is complementary to at least a part of the template.

16. A process according to claim 15, wherein the template is a biological receptor, nucleic acid, cell, virus, microorganism, tissue sample, carbohydrate, oligosaccharide, polysaccharide, nucleoprotein, mucoprotein, lipoprotein, synthetic protein, glycoprotein, glycosaminoglycan, enzyme, steroid, immunosuppressant, hormone, heparin, antibiotic, vitamin or drug.

17. A process according to claim 15, wherein the template is a molecular species having a molecular weight of 200–3,000,000.

18. A process according to claim 15, wherein the functional monomers are selected from the group consisting of amino acids, nucleosides and nucleotides.

19. A process according to claim 15, wherein the functional monomers comprise amino acids and polymerisation is effected by means of an amide-generating condensing agent.

20. A process according to claim 15, in which step (b) comprises (i) separating from the polymerisation system a complex comprising the template molecule and said linear copolymer; and (ii) removal of the template molecule.

21. A process according to claim 20, wherein removal of the template involves separation of the template from the polymer by means of one or more of change in pH of the solution, change in ionic strength of the solution, and/or adding urea, guanidine, or a substance which interacts with the template stronger than does the polymer.

22. A process according to claim 20, wherein removal of the template employs one or more of filtration, electrophoresis, chromatographic separation, washing or centrifugation.

23. A process according to claim 15, wherein step (c) is followed by (d) sequence determination.

24. A process according to claim 23, wherein step (d) is followed by step (e) synthesis of polymers having all or part of the determined sequence and/or variants thereof.

25. A method of making a drug comprising the process of claim 15.

26. A method of making a receptor-specific ligand comprising the process of claim 15.

27. A method comprising admixing a linear copolymer obtained by the process of claim 15 with a pharmaceutical composition.

28. A method comprising admixing a linear copolymer obtained by the process of claim 15 with a food.

* * * * *

UNITED STATES PATENT AND TRADEMARK OFFICE
CERTIFICATE OF CORRECTION

PATENT NO. : 6,852,818 B1
DATED : February 8, 2005
INVENTOR(S) : Piletsky et al.

It is certified that error appears in the above-identified patent and that said Letters Patent is hereby corrected as shown below:

<u>Title page,</u>
Item [75], Inventors, should read
-- [75] Inventors: Sergiy Anatoliyovich Piletsky, Cranfield (GB); Olena Volodimirivna Piletska, Cranfield (GB); Ganna Valentinivna Elska, Kiev (UA); Hakan Sven Andersson, Kalmar (SE); Ian Alan Nicholls, Kalmar (SE); Anthony Peter Francis Turner, North Crawley (GB) --

Signed and Sealed this

Twenty-fourth Day of May, 2005

JON W. DUDAS
*Director of the United States Patent and Trademark Office*